US 11,098,090 B2

(12) United States Patent
Lightfoot et al.

(10) Patent No.: US 11,098,090 B2
(45) Date of Patent: *Aug. 24, 2021

(54) MYCOBACTERIA TUBERCULOSIS CHAPERONIN 60.1 PEPTIDES AND USES THEREOF

(71) Applicant: Revolo Biotherapeutics Limited, Stevenage (GB)

(72) Inventors: Andrew Lightfoot, Stevenage (GB); Nicola Cooper, Stevenage (GB)

(73) Assignee: Revolo Biotherapeutics Limited, Stevenage (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/476,064

(22) PCT Filed: Jan. 11, 2018

(86) PCT No.: PCT/GB2018/050072
§ 371 (c)(1),
(2) Date: Jul. 3, 2019

(87) PCT Pub. No.: WO2018/130834
PCT Pub. Date: Jul. 19, 2018

(65) Prior Publication Data
US 2020/0071365 A1 Mar. 5, 2020

(30) Foreign Application Priority Data
Jan. 12, 2017 (GB) .................................... 1700557

(51) Int. Cl.
*C07K 14/35* (2006.01)
*C07K 7/08* (2006.01)
*A61K 38/00* (2006.01)
*A61K 45/06* (2006.01)

(52) U.S. Cl.
CPC ................ *C07K 14/35* (2013.01); *C07K 7/08* (2013.01); *A61K 38/00* (2013.01); *A61K 45/06* (2013.01)

(58) Field of Classification Search
None
See application file for complete search history.

(56) References Cited

U.S. PATENT DOCUMENTS 9,085,632 B2 * 7/2015 Coates .................... A61P 31/04

FOREIGN PATENT DOCUMENTS

| GB | 2391477 | 2/2004 |
| WO | WO 200240037 A2 | 5/2002 |
| WO | WO 2009/106819 | 9/2009 |
| WO | WO 2013/057499 | 4/2013 |

OTHER PUBLICATIONS

Bowie et al. (Science, 1990, 247:1306-1310.*
Burgess et al. (J. Cell Biol. 111:2129-2138, 1990).*
Lazar et al. (Mol. Cell. Biol., 8:1247-1252, 1988).*
Coin I; Solid-phase peptide synthesis: from standard procedures to the synthesis of difficult sequences, Nature Protocols, 2007, No. 2, vol. 12, pp. 3247-3256.
Fields G.B. and Noble R.L., Solid phase peptide synthesis utilizing 9-fluorenylmethoxycarbonyl amino acids, Int. J. Peptide Protein Res., 1990, 35(3), 161-214.
Hein J. [39] Unified approach to alignment and phylogenies, Methods Enzymology, 1990, vol. 183, pp. 626-645.
Jones J H, A short guide to abbreviations and their use in peptide science, Journal of Peptide Science, 1999, vol. 5, No. 11, pp. 465-471.
Kong T H et al., Mycobacterium tuberculosis expresses two chaperonin-60 homologs, Proc. Natl. Acad. Sci., 1993, 90, 2608-2612.
McDowell R S et al., Structural studies of potent constrained RGD peptides, J. Amer. Chem. Soc., 1992, vol. 114(24), 9245-9253.
Saragovi H U et al., Loops and Secondary Structure Mimetics: Development and Applications in Basic Science and Rational Drug Design, Biotechnology, 1992, vol. 10, pp. 773-778.
Thompson JD et al., Clustal W: improving the sensitivity of prorgressive multiple sequence alignment through sequence . . . , Nucleic Acids Research, 1994, vol. 22(22), pp. 4673-4680.
Lewthwaite et al., "*Mycobacterium tuberculosis* Chaperonin 60.1 Is a More Potent Cytokine Stimulator than Chaperonin 60.2 (Hsp 65)," Infection and Immunity 69:7349-7355 (2001).

* cited by examiner

*Primary Examiner* — Brian Gangle
(74) *Attorney, Agent, or Firm* — Grimes & Yvon LLP

(57) ABSTRACT

The present invention relates to novel peptides derivable from the polypeptide chaperonin 60.1 and to their use in medicine, such as for the prevention and/or treatment of inflammatory conditions.

11 Claims, 7 Drawing Sheets

Specification includes a Sequence Listing.

MYCOBACTERIA TUBERCULOSIS CHAPERONIN 60.1 PEPTIDES AND USES THEREOF

CROSS-REFERENCE TO RELATED APPLICATIONS

This application is the National Stage of International Application No. PCT/GB2018/050072, filed on Jan. 11, 2018, and claims the benefit of priority to GB Application No. 1700557.0, filed on Jan. 12, 2017, both of which are hereby incorporated by referenced in their entireties for all purposes.

The present invention relates to novel peptides derivable from the *Mycobacteria tuberculosis* polypeptide chaperonin 60.1 and to their use in medicine, such as for the prevention and/or treatment of inflammatory conditions.

International Patent Application, Publication Number WO02/040037 discloses pharmaceutical compositions comprising Cpn60.1 from *M. tuberculosis* (MtCpn60.1) and its encoding nucleic acid molecules. This application also discloses a number of specific peptide fragments derivable from the whole length polypeptide which possess similar biological activity. A variety of therapeutic uses for these molecules is also disclosed, including the treatment and/or prevention of autoimmune disorders, allergic conditions, conditions typified by a Th2-type immune response and conditions associated with eosinophilia.

International Patent Application, Publication Number WO2009106819 discloses a series of novel peptides derivable from MtCpn60.1 including a peptide designated as "Peptide 4" having an amino acid sequence: DGSWVNKVSELPAGHGLNVNTLSYGDLAAD (SEQ ID NO: 1). SEQ ID NO: 1 exhibits anti-inflammatory activity and has been shown to significantly reduce the recruitment of eosinophils in an animal model of allergic airway inflammation.

WO2013057499 discloses several sub-fragments of SEQ ID NO: 1 that are shown to possess biological activity.

The present invention is based upon the unexpected finding that certain novel sub-fragments and variants of SEQ ID NO: 1 (DGSVWNKVSELPAGHGLNVNTLSYGDLAAD) exhibit biological activity and an improved pharmacokinetic profile. The novel peptides of the present invention are particularly suited for development as pharmaceuticals owing to their comparatively short amino acid chain length which renders them convenient to prepare and isolate in high yield. They are also indicated to possess improved biological stability in vivo relative to MtCpn60.1 and known peptide fragments thereof. In particular, the peptides claimed herein possess improved half-life.

Accordingly, in an aspect of the invention, the present application provides an isolated or recombinant peptide molecule consisting of an amino acid sequence selected from one of the group (i) to (ix):

(i)
                                        (SEQ ID NO: 2)
XHGLNVNTLSYGD wherein X is absent or is selected from the group consisting of a beta alanine residue, 9-amino-3,6-dioxaoctanoic acid, and an acetyl group; or variants thereof comprising one or more of i(i) to i(iii);
i(i) one or more amino acid residues are in the D conformation,
i(ii) GLNVNTLSYGD (SEQ ID NO: 26) is inverted, or
i(iii) the carboxyl terminal amino acid residue is converted to a primary carboxamide group (ii)
                                        (SEQ ID NO: 3)
DGSVVVNKVSEL-NH2;

(iii)
                                        (SEQ ID NO: 4)
SELPAGHGLNVNTLSYGDLAAD;

(iv)
                                        (SEQ ID NO: 5)
SELPAGHGLNVNTLS;

(v)
                                        (SEQ ID NO: 6)
PAGHGLNVNTLS-NH2;

(vi)
                                        (SEQ ID NO: 7)
VVVNKVSELPAGHGLNVNTLSYGDLAAD;

(vii)
                                        (SEQ ID NO: 8)
NKVSELPAGHGLNVNTLSYGDLAAD;

(viii)
                                        (SEQ ID NO: 9)
PAGHGLNVNTLSYGDLAAD;
and (ix)
                                        (SEQ ID NO: 10)
HGLNVNTLSYGDLAAD or a functionally equivalent fragment or variant thereof.

The present inventors have surprisingly found that the above-mentioned peptides are effective as anti-inflammatory agents whilst at the same time having significantly improved plasma half-life relative to the known peptides derived from chaperonin 60.1 described above.

The peptides of the invention are chemically or recombinantly synthesized and have a number of different chemical, structural and functional properties to the full-length chaperonin 60.1.

By "functionally equivalent" is meant any peptide and/or variant or fragment thereof which possesses a function (e.g. biological activity) that is identical or substantially similar to any function displayed by or attributed to one or more of the defined amino acid sequences (i) to (ix). For example, peptides consisting of the amino acid sequence defined in (i) to (ix) reduce trafficking of eosinophils and/or neutrophils to sites of inflammation, permitting their use in the prevention and/or treatment of a variety of diseases and disorders, including asthma, multiple sclerosis, Crohn's disease, rheumatoid arthritis and inflammatory bowel disease. Functional equivalence in respect of a particular biological activity can be measured using conventional models and methods; for example, by measuring inflammogen induced eosinophil or neutrophil pulmonary influx in sensitized (inflammogen-ovalbumin) or naïve (inflammogen-LPS) animals.

By "variant" is meant a peptide having an amino acid sequence which has or 66% or more, such as 70%, 75%, 80%, 85%, 90% or 95% or more identity to a sequence (i) to (ix) above. Thus the term "variant" refers to polypeptides and peptides differing from naturally occurring molecules by amino acid insertions, deletions, and substitutions, created using, e g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 10 amino acids, more preferably 1 to 5 amino acids, such as 1, 2, 3, 4 or 5 amino acids. The variation allowed may be experimentally determined by systematically making insertions, deletions, or substitutions of amino acids in a polypeptide molecule using recombinant DNA techniques and assaying the resulting recombinant variants for biological activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression.

Fragments of the peptides of the present invention which are capable of exhibiting biological activity are also encompassed by the present invention. Such fragments may be in linear form or they may be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments may be fused to carrier molecules such as immunoglobulins for many purposes, including increasing the valency of protein binding sites.

By "identity" is meant the number or percentage (dependent on presentation of the results) of amino acid residues in a candidate sequence that are identical with the amino acid residues of the sequence of interest, after aligning the sequences and introducing gaps, if necessary to achieve maximum percent sequence identity, and not considering any conservative substitutions as part of the sequence identity.

The percentage sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., (1994) Nucleic Acids Res. 22, 4673-80). The parameters used may be as follows: fast pairwise alignment parameters: K-tuple(word) size; 1, window size; 5, gap penalty; 3, number of top diagonals; 5. Scoring method: x percent; multiple alignment parameters: gap open penalty; 10, gap extension penalty; 0.05. Scoring matrix: BLOSUM.

Sequence identity may be determined, e.g., using the Jotun Hein method (Hein, J. (1990) Methods Enzymol. 183:626-645). Identity between sequences can also be determined by other methods known in the art, e.g. by varying hybridization conditions.

Preferred embodiments of the invention relate to an isolated or recombinant peptide molecule consisting of an amino acid sequence selected from one of the group (a) to (n):

```
(a)
                                          (SEQ ID NO: 11)
XHGLNVNTLSYGD-NH2

(b)
                                          (SEQ ID NO: 12)
XdGysltnvnlGh-NH2;

(c)
                                          (SEQ ID NO: 13)
XhGlnvntlsyGd-NH2;

(d)
                                          (SEQ ID NO: 14)
hGLNVNTLSYGd-NH2;

(e)
                                          (SEQ ID NO: 15)
HGLNVNTLSYGd-NH2;

(f)
                                          (SEQ ID NO: 16)
hGLNVNTLSYGD-NH2;

(g)
                                          (SEQ ID NO: 3)
DGSVVVNKVSEL-NH2;

(h)
                                          (SEQ ID NO: 4)
SELPAGHGLNVNTLSYGDLAAD;

(i)
                                          (SEQ ID NO: 5)
SELPAGHGLNVNTLS;

(j)
                                          (SEQ ID NO: 6)
PAGHGLNVNTLS-NH2;

(k)
                                          (SEQ ID NO: 7)
VVVNKVSELPAGHGLNVNTLSYGDLAAD;

(l)
                                          (SEQ ID NO: 8)
NKVSELPAGHGLNVNTLSYGDLAAD;
```

-continued (m)

PAGHGLNVNTLSYGDLAAD; (SEQ ID NO: 9)
and (n)

HGLNVNTLSYGDLAAD (SEQ ID NO: 10)

wherein upper case denotes an L-amino acid residue, lower case denotes a D-amino acid residue, X is absent or is selected from the group consisting of a beta alanine residue, 9-amino-3,6-dioxaoctanoic acid, and an acetyl group.

The nomenclature for amino acid and peptide derivatives conforms to IUPAC-IUB rules (*J. Peptide Sci.* 1999, 5, 465-471). D-amino acids are indicated by lower-case abbreviations, e.g. Ala or A for L-alanine, ala or a for D-alanine.

The peptides of the invention preferably consist of from 5 to 40 amino acid residues, preferably 5 to 30, most preferably 5 to 20 amino acid residues.

In a preferred embodiment the isolated or recombinant peptide molecule consists of an amino acid sequence HGLNVNTLSYGD-NH2 (SEQ ID NO: 17) or a functionally equivalent fragment or variant thereof.

In a preferred embodiment the isolated or recombinant peptide molecule consists of an amino acid sequence bAla-HGLNVNTLSYGD-NH2 (SEQ ID NO: 18) or a functionally equivalent fragment or variant thereof.

In another preferred embodiment the isolated or recombinant peptide molecule consists of an amino acid sequence Ac-dGysltnvnlGh-NH2 (SEQ ID NO: 19), Ac-hGlnvntl-syGd-NH2 (SEQ ID NO: 20) or a functionally equivalent fragment or variant thereof.

In a further preferred embodiment the present invention provides an isolated or recombinant peptide molecule consisting of an amino acid sequence hGLNVNTLSYGd-NH2 (SEQ ID NO: 14) or a functionally equivalent fragment or variant thereof.

In an additional preferred embodiment the present invention provides an isolated or recombinant peptide molecule consisting of an amino acid sequence HGLNVNTLSYGd-NH2 (SEQ ID NO: 15); or a functionally equivalent fragment or variant thereof.

In a further preferred embodiment provided is isolated or recombinant peptide molecule consisting of an amino acid sequence hGLNVNTLSYGD-NH2 (SEQ ID NO: 16); or a functionally equivalent fragment or variant thereof.

In another preferred embodiment provided is an isolated or recombinant peptide molecule consisting of an amino acid sequence DGSVVVNKVSEL-NH2 (SEQ ID NO: 3); or a functionally equivalent fragment or variant thereof.

MtCpn60.1 may be cloned and expressed using the methods described in T. H. Kong et al., *Proc. Natl. Acad. Sci.*, 1993, 90, 2608-2612 and J. C. Lewthwaite et al, *Infection and Immunity*, 2001, 69(12), 7349-7355. MtCpn60.1 is also commercially available from Lionex (Germany).

The peptides of the present invention may be prepared and/or isolated using conventional methods known in the art. For example, by solution or solid phase synthesis using traditional methods or using a solid phase automated synthesizer, for example as described in I. Coin, *Nature Protocols*, 2007, 2, 3247-3256. Preferably, the peptides of the present invention are prepared by Fmoc solid phase synthesis using methods analogous to those described in G. B. Fields and R. L. Noble, *Int. J. Peptide Protein Res.*, 1990, 35(3), 161-214. Peptides may be cyclized using known methods, for example, as described in H. U. Saragovi, et al., *Bio/Technology* 10, 773-778 (1992) and in R. S. McDowell, et al., *J. Amer. Chem. Soc.* 114, 9245-9253 (1992), both of which are incorporated herein by reference. Such peptides may be fused to carrier molecules such as immunoglobulins for many purposes, including increasing the valency of protein binding sites.

It is understood that the compounds of the invention include salts. Metabolites and pro-drugs are also included. The compounds according to the invention also include any isotopic derivatives.

The peptides may be used according to the invention when the patient is further administered one or more therapeutic agents or when the peptides are provided in combination with one or more therapeutic agents. The therapeutic agent may be selected from, but not limited to, disease modifying agents, including biological immunomodulators, analgesics, broncodilators, anti-inflammatory agents, anti-allergic drugs, allergen immunotherapy, antivirals, antibiotics, antibodies, steroids and drugs commonly used in the treatment of any of the chronic and relapsing-remitting conditions according to the invention.

Disease modifying agents include for example hydroxychloroquine, sulfasalazine, leflunamide, methotrexate and minocycline and biologics which target TNFalpha, such as abatacept, adalimumab, etanercept, infliximab and golimumab, or immunomodulators such as alemtuzumab, interferon beta-1b, beta interferon-1a dimethyl fumarate, copaxone, natalizumab and teriflunomide. Analgesics include, paracetamol, non steroidal anti-inflammatory drugs such as ibuprofen and aspirin, codeine, tramadol, morphine, amitriptyline, gabapentin and opiates.

Anti-inflammatory agents include leukotriene receptor antagonists, theophylline and PDE4 inhibitors such as roflumilast, low, medium and high dose corticosteroids, via inhalation, sub cutaneous, intramuscular, sublingual, intravenous and oral dosing. Antivirals include oseltamivir. Antibiotics include arnoxicillin. Antibodies include anti-IgE antibodies (e.g. omaluzimab), antibodies which modify cytokine signaling (e.g. anti-IL-5mab mepoluzimab). Steroids include fluticasone propionate and fluticasone furorate, beclomethasone dipropionate, budesonide, ciclesonide, flunisolide, and mometasone. The use according to the invention when the further one or more therapeutic agents are selected from corticosteroids, anti-leukotrienes, cytokine monoclonal antibodies or theophylline may be preferred. Use when the further agent is a bronchodilator may also be preferred. Preferred bronchodilators include, short acting B2 agonists such as salbutamol, long acting B2 agonists such as salmeterol, formoterol, olodaterol and vilanterol, short acting rnuscarinic receptor antagonists such as ipratropium bromide and long acting muscarinic receptor antagonists such as aclidinum bromide, tiotropium bromide, and glycopyrronium bromide.

Uses of the Peptides

According to a further aspect of the present invention there is provided a peptide as defined herein for use in medicine or veterinary medicine.

The peptide of the invention may be for use in a human or non-human animal, typically a mammal.

Preferably, the peptide of the present invention is used for the treatment and/or prevention of acute and/or chronic inflammatory conditions. Preferred examples of acute and/or chronic inflammatory conditions include inflammation associated with infection (such as septic shock, sepsis or systemic inflammatory response syndrome (SIRS)), ischemia-reperfusion injury including coronary thrombosis and cerebral artery blockage, shock lung syndrome, endotoxin lethality, arthritis (particularly rheumatoid arthritis or chronic inflammatory arthritis), complement-mediated hyperacute rejection, nephritis, cytokine or chemokine-induced lung injury, non-allergic asthma, allergic asthma, allergic rhinitis, atopic dermatitis, cystic fibrosis, pulmonary fibrosis, inflammatory bowel disease, Crohn's disease and ulcerative colitis.

Further preferred inflammatory conditions include; acute organ failure associated with surgery, such as acute kidney injury, acute respiratory distress syndrome associated with the following surgical interventions (not exhaustive list); cardiac surgery, coronary artery bypass, aortic aneurysm, valve surgery, oesophagectomy, kidney diseases, coronary artery bypass grafting, aortic root and ascending aortic aneurysm repair surgery.

In an alternative embodiment, the present invention provides the use of a peptide as defined herein for the prevention and/or treatment of chronic obstructive pulmonary disease.

In an alternative embodiment, the present invention provides the use of a peptide as defined herein for the prevention and/or treatment of autoimmune disorders.

Within the term "autoimmune disorders" as used herein are included conditions where it can be shown that the autoimmune process contributes to the pathogenesis of a disease. Such disorders are typically associated with a T helper lymphocyte-1 (Th-1) type immune response.

Examples of autoimmune disorders which may be prevented and/or treated with the peptide molecules of the present invention include autoimmune disorders, such as haemolytic anaemia, thrombocytopenia, pernicious anaemia, Addison's disease, autoimmune diabetes, insulin dependent diabetes mellitus, myasthenia gravis, rheumatoid arthritis, systemic lupus erythematosus, atherosclerosis, autoimmune encephalitis, connective tissue disease, multiple sclerosis, autoimmune pulmonary inflammation, Guillain-Barre syndrome, autoimmune thyroiditis, graft-versus-host disease and autoimmune inflammatory eye disease. Preferred autoimmune disorders include rheumatoid arthritis and multiple sclerosis.

In an alternative embodiment, the present invention provides the use of a peptide as defined herein for the prevention and/or treatment of allergic conditions. Examples of allergic conditions and disorders which may be prevented and/or treated with the peptide molecules of the present invention include eczema, dermatitis, allergic rhinitis (hay fever), allergic airways diseases, hyper-eosinophilic syndrome, contact dermatitis; respiratory diseases characterized by eosinophilic airway inflammation and airway hyper-responsiveness, such as asthma, including allergic asthma and intrinsic asthma, allergic bronchopulmonary aspergillosis, eosinophilic pneumonia, allergic bronchitis bronchiectasis, occupational asthma, reactive airway disease syndrome, interstitial lung disease, hyper-eosinophilic syndrome, parasitic lung disease; anaphylaxis, serum sickness, drug reactions, food allergies, insect venom allergies, mastocytosis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis and giant papillary conjunctivitis. Other conditions, in which immunomodulation is desired (including, for example, organ transplantation), may also be treatable using a peptide molecule of the present invention. Preferred allergic disorders and conditions include asthma, allergic rhinitis, and atopic dermatitis.

Within the terms "allergic disorders" and "allergic conditions" as used herein are included conditions associated with a T helper lymphocyte-2 (Th-2) type immune response. In allergic reaction, high IgE levels occur and Th-2 immune responses predominate over Th-1 responses, resulting in inflammatory response.

WO2013057499 discloses suitable assays for assessing;
(a) the therapeutic effects of the polypeptides or antagonists thereof on allergic reactions,
(b) thymocyte or splenocyte cytotoxicity
(c) T-cell-dependent immunoglobulin responses and isotype switching (which will identify, among others, proteins that modulate T-cell dependent antibody responses and that affect Th1/Th2 profiles),
(d) mixed lymphocyte reaction (MLR) assays (which will identify, among others, proteins that generate predominantly Th1 and CTL responses),
(e) dendritic cell-dependent assays (which will identify, among others, proteins expressed by dendritic cells that activate naive T-cells),
(f) lymphocyte survival/apoptosis (which will identify, among others, proteins that prevent apoptosis after superantigen induction and proteins that regulate lymphocyte homeostasis),
(g) proteins that influence early steps of T-cell commitment and development
(h) immunomodulatory effects of the peptide molecules of the present invention against rheumatoid arthritis may be determined in an experimental animal model system.

As used herein "treatment" means reducing, alleviating or eliminating one or more symptoms of the condition which is being treated, relative to the symptoms prior to treatment. For example, symptoms which may be affected include eosinophilia, decreased secretion of particular cytokines, a Th2-based immune response, allergic response and the presence of autoantibodies.

As used herein "prevention" means delaying or preventing the onset of a condition or reducing its severity, as assessed by the appearance or extent of one or more symptoms of said condition.

The invention further provides a method of preventing and/or treating a condition as defined above which comprises administering to a mammal, including man, a peptide as defined herein.

The invention still further provides the use of a peptide as defined herein in the manufacture of a medicament for the prevention and/or treatment of a condition as defined above.

Pharmaceutical Compositions

In an additional aspect the present invention provides a pharmaceutical composition comprising a peptide molecule as defined above and one or more pharmaceutically acceptable excipients for use in a method as defined above.

The compounds described herein may be formulated for administration in any convenient way. The present invention provides a pharmaceutical composition comprising a peptide molecule as defined above and one or more pharmaceutically acceptable excipients for use in a method as defined above.

Any suitable route of administration can be used. For example, any of oral, topical, parenteral, ocular, rectal, vaginal, inhalation, buccal, sublingual and intranasal delivery routes may be suitable.

The peptide molecules and pharmaceutical compositions of the invention can be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The medicaments and compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The molecules, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a agent of the invention and a suitable powder base such as lactose or starch.

Aerosol or dry powder formulations are preferably arranged so that each metered dose or "puff" contains at least 200 pg of a molecule of the invention for delivery to the patient. It will be appreciated that the overall daily dose with an aerosol will vary from patient to patient, and may be administered in a single dose or, more usually, in divided doses throughout the day.

The peptide molecules and pharmaceutical compositions of the invention can also be delivered orally. The process may employ a natural process for oral uptake of vitamin $B_{12}$ and/or vitamin D in the body to co-deliver proteins and peptides. By riding the vitamin $B_{12}$ and/or vitamin D uptake system, the nucleic acids, molecules and pharmaceutical formulations of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The peptide molecules and pharmaceutical compositions of the invention will normally be administered by any parenteral route or intranasally, and in some embodiments orally, in the form of a pharmaceutical composition comprising the active ingredient. Depending upon the disorder and patient to be treated, as well as the route of administration, the compositions may be administered at varying doses.

In human therapy, the peptide molecules and pharmaceutical compositions of the invention can be administered alone but will generally be administered in admixture with a suitable pharmaceutical excipient, diluent or carrier selected with regard to the intended route of administration and standard pharmaceutical practice.

Preferably, the pharmaceutical composition of the present invention is a unit dosage containing a daily dose or unit, daily sub-dose or an appropriate fraction thereof, of the active ingredient.

For example, the peptide molecules and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The peptide molecules and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, and glyceryl behenate may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents of the invention may be combined with various sweetening or flavouring agents, colouring matter or dyes, with emulsifying and/or suspending agents and with diluents such as water, ethanol, propylene glycol and glycerin, and combinations thereof.

For oral and parenteral administration to human patients, the daily dosage level of the molecules, medicaments and pharmaceutical compositions of the invention will usually be from 200 pg to 100 mg per adult per day administered in single or divided doses.

Thus, for example, the vial, the tablets or capsules of the molecules of the invention may contain from 200 pg to 100 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Alternatively, the molecules, medicaments and pharmaceutical compositions of the invention can be administered in the form of a suppository or pessary, or they may be applied topically in the form of a lotion, solution, cream, gel, ointment or dusting powder. The molecules, medicaments and pharmaceutical compositions of the invention may also be transdermally administered, for example, by the use of a skin patch. They may also be administered by the ocular route, particularly for treating diseases of the eye.

For ophthalmic use, the molecules, medicaments and pharmaceutical compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the molecules, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

For veterinary use, the molecules, medicaments and pharmaceutical compositions of the invention is administered as a suitably acceptable formulation in accordance with normal veterinary practice and the veterinary surgeon will determine the dosing regimen and route of administration which will be most appropriate for a particular animal.

Conveniently, the formulation is a pharmaceutical formulation. Advantageously, the formulation is a veterinary formulation.

Advantageously, in the use according to the invention, the daily dosage level will be from 10 pg to 100 mg. Preferably the daily dosage level will be from 20 pg to 50 mg, 20 pg to 10 mg or 20 pg to 8 mg, administered in single or divided doses.

Preferred pharmaceutical formulations include those in which the active ingredient is present in at least 0.000001% up to 5% by weight. That is, the ratio of active ingredient to the other components (i.e. the addition of adjuvant, diluent and carrier) of the pharmaceutical composition is at least 1:99 (e.g. at least 10:90, preferably at least 30:70 and most preferably at least 50:50) by weight.

Preferably, the pharmaceutical composition or the medicament of the invention is formulated to permit administration by at least one route selected from the group comprising or consisting of: intranasal; oral; parenteral; topical; ophthalmic; suppository; pessary; or inhalation routes. Formulations suitable for such administration routes are well known to those in the art of pharmacy and medicine and exemplary formulations are described above and in the accompanying examples.

Typically, the time between dose administration to the patient is between six and twelve hours; in a preferred embodiment, the time between dose administration to the patient is between nine and twelve hours after the previous dose; more preferably, the time between dose administration to the patient is between twelve hours and twelve days; even more preferably, the time between dose administration to the patient is between twelve days and six months.

Preferably, the pharmaceutical composition or the medicament of the invention is formulated to permit administration by at least one route selected from the group comprising or consisting of: intranasal; sub-lingual, oral; parenteral; topical; ophthalmic; suppository; pessary; or inhalation routes. Formulations suitable for such administration routes are well known to those in the art of pharmacy and medicine and exemplary formulations are described above and in the accompanying examples.

DESCRIPTION OF FIGURES

Non-limiting examples will now be described with reference to the following figures.

EXAMPLES

Example 1

Synthesis

Figure 1:
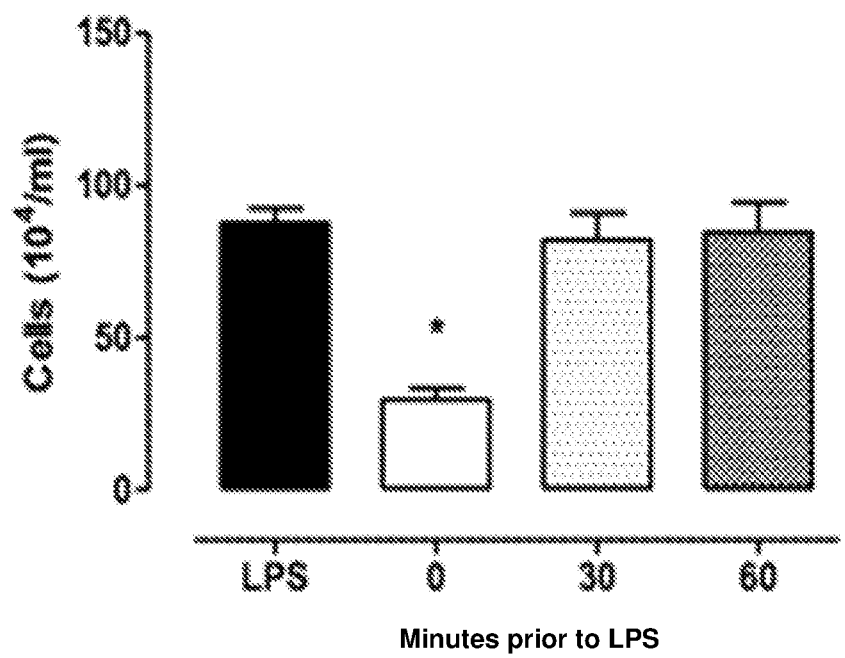
FIG. 1 shows the effect of SEQ ID NO: 1 (0.5 pg/mouse i.v) on LPS induced lung neutrophil influx in the mouse when SEQ ID NO: 1 is administered at 0, 30 and 60 minutes prior to administration of LPS.

Synthesis and purification used automated Fluorenylmethoxycarbonyl solid phase peptide synthesis (Fmoc SPSS). Peptides were synthesized on 2-Chlorotrityl or TentaGel resins, derivatized with one of a number of cleavable linkers, using an Fmoc/t-butyl-based solid-phase synthesis strategy. Temporary N-amino group protection was afforded by the Fmoc-group, with t-butyl ethers being used for protection of tyrosine, serine, and threonine hydroxyl side chains, whereas t-butyl esters protected the side chains of aspartic and glutamic acid residues. Histidine and lysine side chains were protected as their N-trityl and N-Boc derivatives, respectively, cysteine as its S-trityl derivative and arginine guanidine moiety as its Pbf derivative.

Upon completion of the synthesis, peptides were cleaved from the solid support, with removal of side chain protecting groups, by treatment with trifluoroacetic acid (TFA) containing triisobutylsilane and water as scavengers. After removal of TFA and scavengers by evaporation and trituration in diethyl ether, peptide purification was performed by reversed-phase preparative HPLC, followed by lyophilization. The purified product was subsequently analyzed by reverse-phase HPLC and by mass spectrometry.

Example 2

Activity of new peptides in an LPS model of inflammation SEQ ID NO: 3 is a peptide in accordance with the invention which is a fragment of the peptide SEQ ID NO: 1 (Table 1) (peptide 4 disclosed in WO2009/106819).

TABLE 1

Amino Acid Sequences of SEQ ID NO: 1 and SEQ ID NO: 3

| SEQ ID No. | Peptide Sequence |
|---|---|
| SEQ ID NO: 1 (comparative example) | DGSVVVNKVSELPAGHGLNVNTLSYGDLAAD |
| SEQ ID NO: 3 | DGSVVVNKVSEL-NH2 |

LPS Mouse Method

BALB/c female and male mice, 6 to 8 weeks old (Harlan, UK) received 25 pg/mouse of *E. Coli* lipopolysaccharide (LPS) intranasally immediately after receiving intranasal peptide diluted in sterile saline or saline only. 4 hours later mice were euthanized with an overdose of urethane and a cannula inserted into the exposed trachea and three 0.5 ml aliquots of saline were injected into the lungs. From the BAL (bronchoalveolar lavage) fluid, an aliquot (50 µl) was added to 50 µl of haemolysis solution (Turk's solution, Fluka, UK). The total number of cells in the lavage was counted with an improved Neubauer haemocytometer. For differential cell counts, cytospin preparations were prepared from aliquots of BAL fluid (100 µL) centrifuged at 1000 rpm for 1 min at room temperature. Cells were stained with Diff Quick and a total of 100 cells were counted to determine the proportion of neutrophils, eosinophils and monocytes using standard morphological criteria.

SEQ ID NO: 1 is extremely potent in the mouse LPS model when dosed intravenously immediately prior to LPS challenge showing a significant inhibition of LPS induced lung neutrophil influx. SEQ ID NO: 1 looses its activity in this model however when given at earlier (FIG. 1) or later (FIG. 4) time points.

Figure 2:
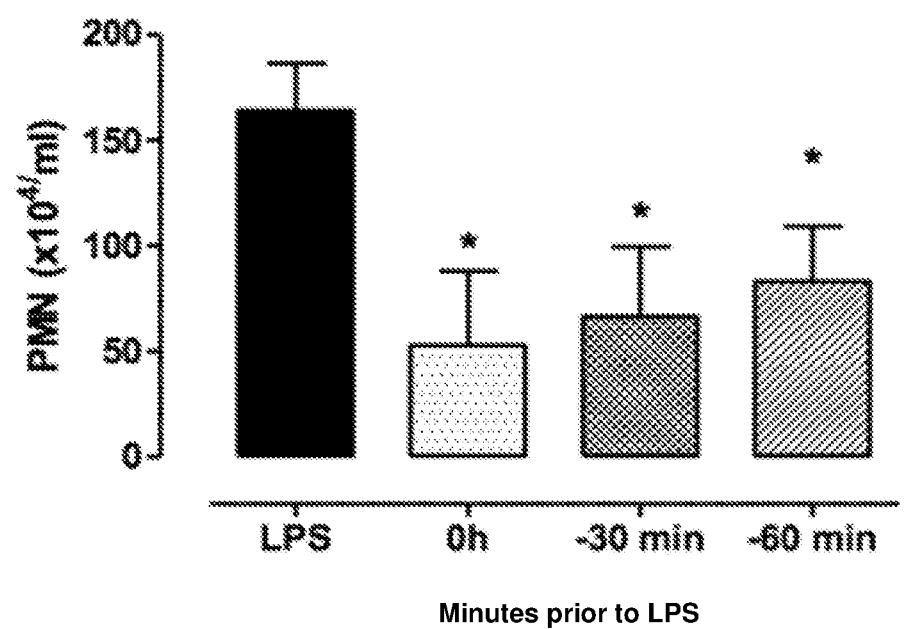
FIG. 2 shows the effect of SEQ ID NO: 3 (50 pg/mouse i.v) on LPS induced lung neutrophil influx in the mouse when SEQ ID NO: 3 is administered at 0, 30 and 60 minutes prior to administration of LPS.
Figure 3:
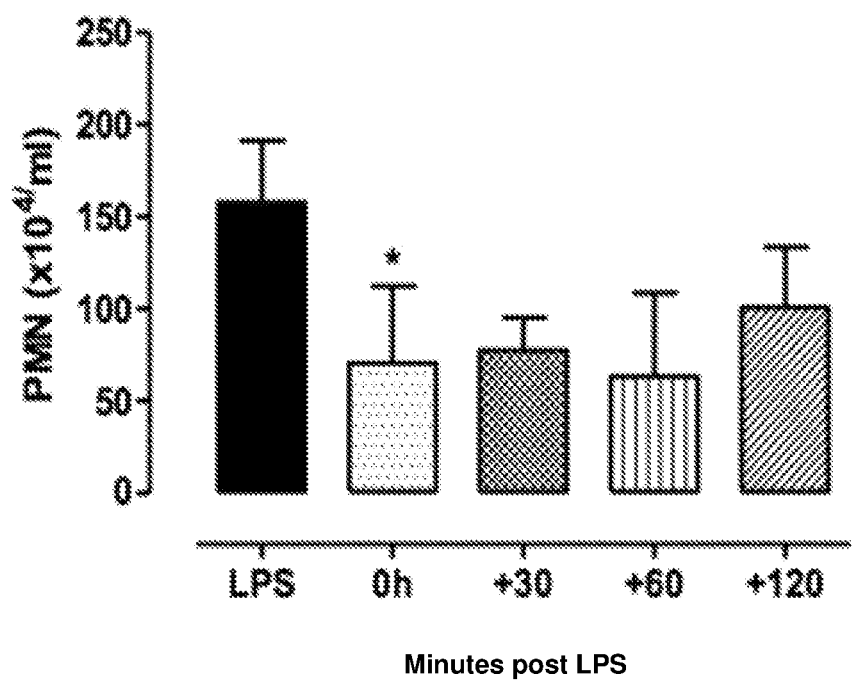
FIG. 3 shows the effect of SEQ ID NO: 3 (50 pg/mouse i.v) on LPS induced lung neutrophil influx in the mouse when SEQ ID NO: 3 is administered at 0, 30, 60 and 120 minutes post administration of LPS.
Figure 4:
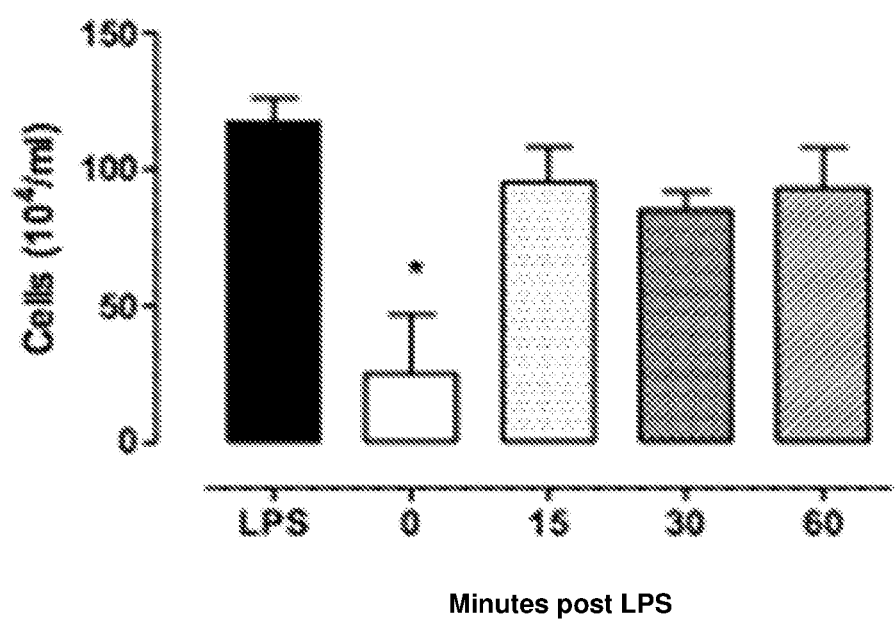
FIG. 4 shows the effect of SEQ ID NO: 1 (50 pg/mouse i.v) on LPS induced lung neutrophil influx in the mouse when SEQ ID NO: 1 is administered at 0, 30, 60 and 120 minutes post administration of LPS.

A fragment of SEQ ID NO: 1, SEQ ID NO: 3 is effective in the LPS mouse model when dosed intravenously. Surprisingly SEQ ID NO: 3 is also efficacious in this model against LPS induced lung neutrophil influx when dosed up to 60 mins prior to LPS challenge (FIG. 2) and up to 120 mins post LPS challenge (FIG. 3) unlike SEQ ID NO: 1, which only demonstrates efficacy when dosed immediately prior to LPS challenge (FIGS. 1 and 4).

Conclusion

The extended dosing options for SEQ ID NO: 3 allow for both therapeutic and prophylactic, dosing protocols to be employed clinically. This profile extends the number of indications able to be treated with this peptide.

Example 3

Small fragments of SEQ ID NO: 1 Showing Significant Improvement in Plasma Stability Many peptides have poor plasma stability due to metabolism by proteases. A small peptide fragment of SEQ ID NO: 1 (peptide 4 in WO2009/106819) was synthesized and tested for efficacy in the LPS mouse lung neutrophilia model and for plasma stability in mouse, rat and human plasma (SEQ ID NO: 17). Modifications of this peptide were then made and the resulting molecules tested in the same systems.

TABLE 2

Amino Acid Sequences of SEQ ID NOs: 17, 21, 22 and 18

| SEQ ID No. | Peptide Sequence |
|---|---|
| SEQ ID NO: 17 | HGLNVNTLSYGD-NH2 |
| SEQ ID NO: 21 | HGLNVNTLSYGD-bAla-NH2 |
| SEQ ID NO: 22 | bAla-HGLNVNTLSYGD-bAla-NH2 |
| SEQ ID NO: 18 | bAla-HGLNVNTLSYGD-NH2 |

Plasma Stability in Mouse, Rat and Human Plasma at 37° C.

Plasma: mouse (C57 Black 6 Male), rat (Sprague Dawley) and human containing heparin as an anti-coagulant.

Plasma samples in duplicate were incubated with peptide at 3 µM in a 600 µl volume at 37° C. with shaking. 50 µl aliquots were withdrawn after 2, 5, 30, 60 and 120 mins and quenched into 150 µl of ice-cold methanol containing the internal standard (tolbutamide). Samples were stored at −20° C. for 2 hours to allow protein precipitation. Samples were then centrifuged at 2500×g and the resulting supernatants transferred to a 96 well plate for LC-MS/MS analysis. $T_{half}$ was calculated in all matrices for each peptide.

Results

TABLE 3

Plasma Stability Results for SEQ ID NOs: 17, 21, 22 and 18

| | | Plasma Half Life (Th) (mins) | | |
|---|---|---|---|---|
| SEQ ID NO. | Peptide Sequence | Mouse | Rat | Man |
| SEQ ID NO: 17 | HGLNVNTLSYGD-NH2 | 20 | 43 | 72 |
| SEQ ID NO: 21 | HGLNVNTLSYGD-bAla-NH2 | 107 | 75 | 151 |
| SEQ ID NO: 22 | bAla-HGLNVNTLSYGD-bAla-NH2 | >360 | >360 | >360 |
| SEQ ID NO: 18 | bAla-HGLNVNTLSYGD-NH2 | 37 | >360 | 171 |

Addition of a beta-alanine group, at either the N-terminus (SEQ ID NO: 18) the C-terminus (SEQ ID NO: 21) or both termini (SEQ ID NO: 22) improved the plasma stability of the peptides.

Figure 5:
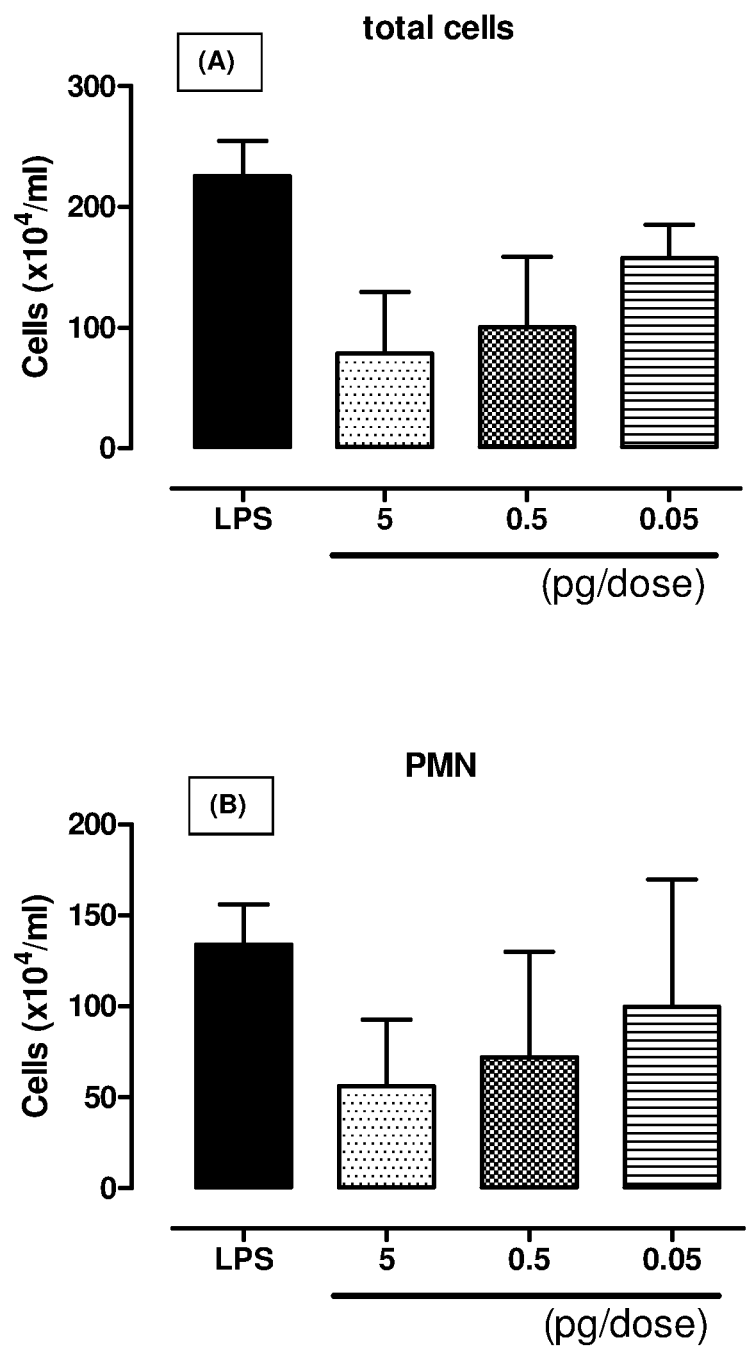
FIG. 5 shows the effect of SEQ ID NO: 17 (0.05, 0.5 and 5 pg/dose) on LPS induced neutrophil influx to the mouse lung.
Figure 6:
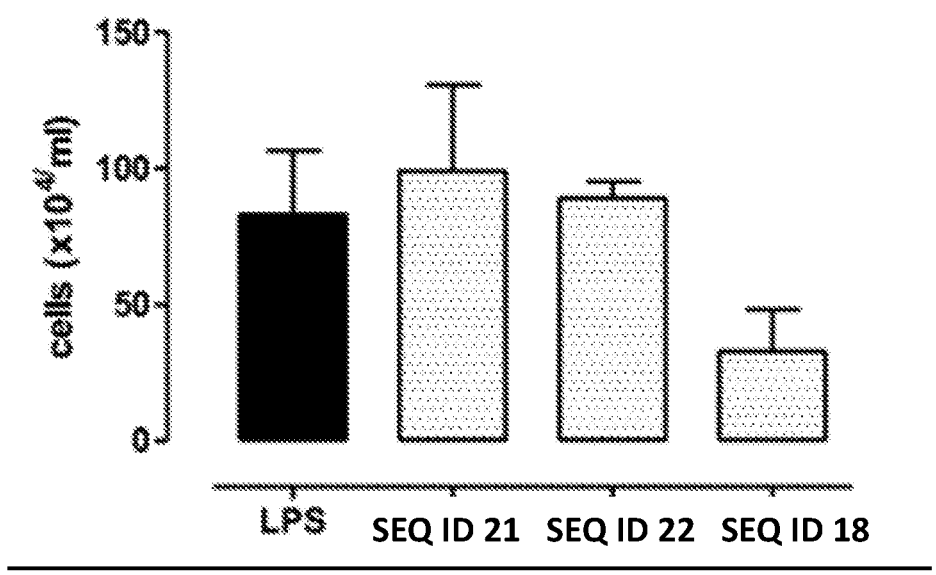
FIG. 6 shows the effect of SEQ ID NOs: 21, 22 and 18 (50 pg/mouse) on LPS induced neutrophil influx to the mouse lung.
Figure 7:
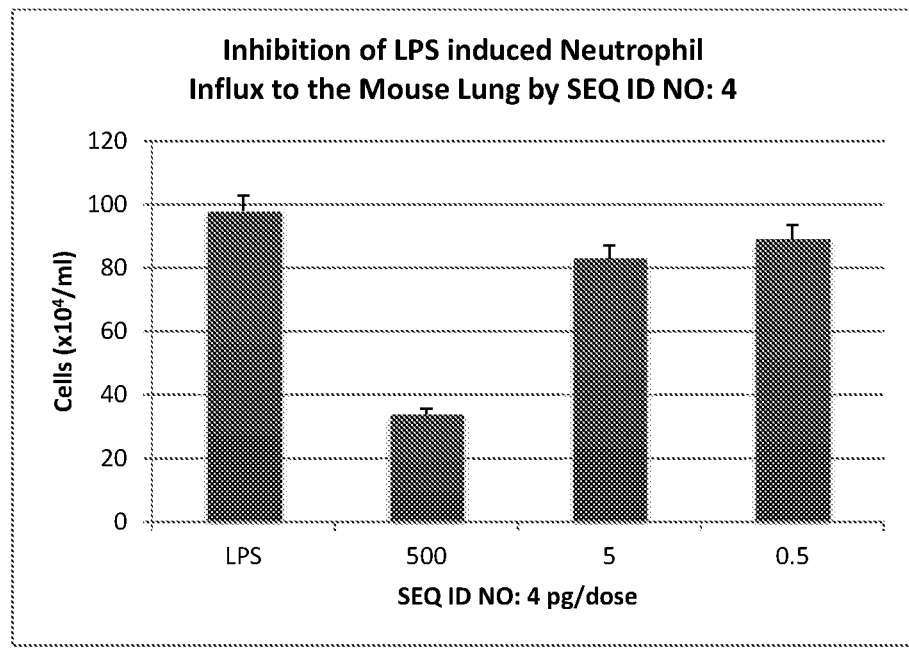
FIG. 7 shows the effect of SEQ ID NO: 4 (0.5, 5 and 500 pg/dose) on LPS induced neutrophil influx to the mouse lung.

FIGS. 5, 6 and 7 show the results of testing the peptides in the LPS mouse method as described above for Example 2.

FIGS. 5 and 6 show the effect of SEQ ID NO: 17 on LPS induced lung neutrophil influx in the mouse, with a reduction in the number of neutrophils on administration of different doses of SEQ ID NO: 17 (0.5, 5 or 50 pg/mouse).

FIG. 7 shows the effect of SEQ ID NOs: 21, 22 and 18 (50 pg/mouse, i.v) on LPS induced lung neutrophil influx in the mouse.

SEQ ID NO: 18 retains anti-inflammatory activity in the LPS mouse model whilst showing a significant improvement in plasma half-life (Th) over the parent peptide SEQ ID NO: 17 in mouse, rat and human plasma (Table 3). SEQ ID NO: 21 and SEQ ID NO: 22 show superior Th to SEQ ID NO: 17 but loose efficacy in the LPS mouse lung inflammation model. Accordingly, addition of a beta-alanine group at the C-terminal only improves plasma stability whilst preserving efficacy.

Example 4

Table 4 shows plasma stability data in 3 species for SEQ ID NO: 23 and SEQ ID NO: 5: (peptide fragments 2 and 3 from WO2013057499).

TABLE 4

| | Plasma half life (mins) | | |
|---|---|---|---|
| | Mouse | Rat | Man |
| GLNVNTLSYGDLAAD (SEQ ID NO: 23) | 62 | >308 | >337 |
| SELPAGHGLNVNTLS (SEQ ID NO: 5) | 12 | 79 | 111 |

A longer fragment (SEQ ID NO: 4) was synthesized, an extended form of fragment 3 and tested for plasma stability. This fragment showed a superior half-life (Table 5) and maintained in vivo efficacy in the mouse LPS lung inflammation model (FIG. 7).

TABLE 5

| | | Plasma half-life (mins) | | |
|---|---|---|---|---|
| Peptide | | Mouse | Rat | Man |
| SEQ ID NO: 4 | SELPAGHGLNVNTLSYGDLAAD | >360 | >360 | >360 |

Example 5

Plasma Stability of Modified Peptides

Structural modifications were then made to peptide SEQ ID NO: 17 to improve plasma stability as set out in Table 6. The plasma stability of the peptides was then assessed under the same conditions as outlined above.

TABLE 6

| Peptide | Sequence |
|---|---|
| SEQ ID NO: 17 | HGLNVNTLSYGD-NH2 |
| SEQ ID NO: 24 | O2Oc-HGLNVNTLSYGD-NH2 |
| SEQ ID NO: 21 (Comparative) | HGLNVNTLSYGD-bAla-NH2 |
| SEQ ID NO: 22 (Comparative) | bAla-HGLNVNTLSYGD-bAla-NH2 |
| SEQ ID NO: 18 | bAla-HGLNVNTLSYGD-NH2 |
| SEQ ID NO: 19 | Ac-dGysltnvnlGh-NH2 |
| SEQ ID NO: 20 | Ac-hGlnvntlsyGd-NH2 |
| SEQ ID NO: 14 | hGLNVNTLSYGd-NH2 |
| SEQ ID NO: 15 | HGLNVNTLSYGd-NH2 |
| SEQ ID NO: 16 | hGLNVNTLSYGD-NH2 |
| SEQ ID NO: 25 | cyclic-HGLNVNTLSYGD- |

The plasma half lives for the above-mentioned peptides in mouse, rat or human are set out in Table 7.

TABLE 7

| | | Plasma half life (mins) | | |
|---|---|---|---|---|
| Peptide | | Mouse | Rat | Man |
| SEQ ID NO: 17 | HGLNVNTLSYGD-NH2 | 20 | 43 | 72 |
| SEQ ID NO: 24 | O2Oc-HGLNVNTLSYGD-NH2 | 51 | >360 | 259 |
| SEQ ID NO: 21 (Comparative) | HGLNVNTLSYGD-bAla-NH2 | 107 | 75 | 151 |
| SEQ ID NO: 22 (Comparative) | bAla-HGLNVNTLSYGD-bAla-NH2 | >360 | >360 | >360 |
| SEQ ID NO: 18 | bAla-HGLNVNTLSYGD-NH2 | 37 | >360 | 171 |
| SEQ ID NO: 19 | Ac-dGysltnvnlGh-NH2 | >360 | >360 | >360 |
| SEQ ID NO: 20 | Ac-hGlnvntlsyGd-NH2 | >360 | 182 | >360 |
| SEQ ID NO: 14 | hGLNVNTLSYGd-NH2 | 50 | 153 | 155 |
| SEQ ID NO: 15 | HGLNVNTLSYGd-NH2 | 39 | 182 | 84 |

TABLE 7-continued

| Peptide | | Plasma half life (mins) | | |
|---|---|---|---|---|
| | | Mouse | Rat | Man |
| SEQ ID NO: 16 | hGLNVNTLSYGD-NH2 | 35 | 200 | 111 |
| SEQ ID NO: 25 | cyclic-HGLNVNTLSYGD- | 10 | 21 | 45 |

Addition of a beta-alanine group to one end of SEQ ID NO: 17 significantly improved plasma stability whilst activity was maintained, whilst addition of the group to both ends improved the stability even further (see SEQ ID NO: 22) but resulted in a loss of biological activity. Beta-alanine addition is known to enhance the ability of synthetic protein fragments to survive the degradative action of aminopeptidases and serum proteolytic enzymes.

Reconfiguring the fragment using d-configuration, amino acids (SEQ ID NOs: 19 and 20), which are seldom found in living organisms shows enhanced plasma stability likely also to be due to enhanced protection from proteolysis by aminopeptidases and serum proteolytic enzymes. Addition of N-terminal acetylation to these peptides, known to have stabilising activity further added to the improvement in plasma stability.

Surprisingly cyclisation (SEQ ID NO: 25), one of the most widely used methods to increase the conformational stability of peptides did not improve plasma stability.

The invention claimed is:

1. An isolated or recombinant peptide molecule consisting of an amino acid sequence selected from one of the group (i) to (viii):

(i)
(SEQ ID NO: 2)
XHGLNVNTLSYGD wherein X is absent or is selected from the group consisting of a beta alanine residue, 9-amino-3,6-dioxaoctanoic acid, and an acetyl group; or variants thereof comprising one or more of i(i) to i(iii);
  i(i) one or more amino acid residues are in the D conformation,
  i(ii) GLNVNTLSYGD (SEQ ID NO: 26) is inverted, or
  i(iii) the carboxyl terminal amino acid residue is converted to a primary carboxamide group (ii)
(SEQ ID NO: 3)
DGSVVVNKVSEL-NH2;

(iii)
(SEQ ID NO: 4)
SELPAGHGLNVNTLSYGDLAAD;

(iv)
(SEQ ID NO: 5)
SELPAGHGLNVNTLS;

(v)
(SEQ ID NO: 6)
PAGHGLNVNTLS-NH2;

(vi)
(SEQ ID NO: 7)
VVVNKVSELPAGHGLNVNTLSYGDLAAD;

(vii)
(SEQ ID NO: 8)
NKVSELPAGHGLNVNTLSYGDLAAD;

(viii)
(SEQ ID NO: 9)
PAGHGLNVNTLSYGDLAAD;
and (ix)
(SEQ ID NO: 10)
HGLNVNTLSYGDLAAD.

2. The isolated or recombinant peptide molecule according to claim 1, consisting of an amino acid sequence selected from one of the group (a) to (m):

(a)
(SEQ ID NO: 11)
XHGLNVNTLSYGD-NH2

(b)
(SEQ ID NO: 12)
XdGysltnvnlGh-NH2;

(c)
(SEQ ID NO: 13)
XhGlnvntlsyGd-NH2;

(d)
(SEQ ID NO: 14)
hGLNVNTLSYGd-NH2;

(e)
(SEQ ID NO: 15)
HGLNVNTLSYGd-NH2;

(f)
(SEQ ID NO: 16)
hGLNVNTLSYGD-NH2;

(g)
(SEQ ID NO: 3)
DGSVVVNKVSEL-NH2;

(h)
(SEQ ID NO: 4)
SELPAGHGLNVNTLSYGDLAAD;

(i)
(SEQ ID NO: 5)
SELPAGHGLNVNTLS;

(j)
(SEQ ID NO: 6)
PAGHGLNVNTLS-NH2;

(k)
(SEQ ID NO: 7)
VVVNKVSELPAGHGLNVNTLSYGDLAAD;

(l)
(SEQ ID NO: 8)
NKVSELPAGHGLNVNTLSYGDLAAD;

(m)
(SEQ ID NO: 9)
PAGHGLNVNTLSYGDLAAD;
and (n)
(SEQ ID NO: 10)
HGLNVNTLSYGDLAAD;

wherein upper case denotes an L-amino acid residue, lower case denotes a D-amino acid residue, X is absent or is selected from the group consisting of a beta alanine residue, 9-amino-3,6-dioxaoctanoic acid, and an acetyl group.

3. The isolated or recombinant peptide molecule according to claim 1, consisting of an amino acid sequence HGLNVNTLSYGD-NH2 (SEQ ID NO: 17).

4. The isolated or recombinant peptide molecule according to claim 1, consisting of an amino acid sequence bAla-HGLNVNTLSYGD-NH2 (SEQ ID NO: 18).

5. The isolated or recombinant peptide molecule according to claim 1, consisting of an amino acid sequence Ac-dGysltnvnlGh-NH2 (SEQ ID NO: 19), Ac-hGlnvntlsyGd-NH2 (SEQ ID NO: 20).

6. The isolated or recombinant peptide molecule according to claim 1, consisting of an amino acid sequence hGLNVNTLSYGd-NH2 (SEQ ID NO: 14) or a functionally equivalent fragment or variant thereof; or an amino acid sequence HGLNVNTLSYGd-NH2 (SEQ ID NO: 15).

7. The isolated or recombinant peptide molecule according to claim 1, consisting of an amino acid sequence hGLNVNTLSYGD-NH2 (SEQ ID NO: 16) or a functionally equivalent fragment or variant thereof; or an amino acid sequence DGSVVVNKVSEL-NH2 (SEQ ID NO: 3).

8. A pharmaceutical composition comprising the peptide molecule according to claim 1 and one or more pharmaceutically-acceptable excipients.

9. The pharmaceutical composition according to claim 8, further comprising one or more additional therapeutic agents.

10. The pharmaceutical composition according to claim 9, wherein the additional therapeutic agent is selected from disease modifying agents, analgesics, broncodilators, anti-inflammatory agents, anti-allergic drugs, allergen immunotherapeutic agents, antivirals, antibiotics, antibodies and steroids.

11. The pharmaceutical composition according to claim 9, wherein the additional therapeutic agent is selected from corticosteroids, anti-leukotrienes, cytokine monoclonal antibodies and theophylline.

* * * * *

UNITED STATES PATENT AND TRADEMARK OFFICE
CERTIFICATE OF CORRECTION

PATENT NO. : 11,098,090 B2
APPLICATION NO. : 16/476064
DATED : August 24, 2021
INVENTOR(S) : Andrew Lightfoot and Nicola Cooper It is certified that error appears in the above-identified patent and that said Letters Patent is hereby corrected as shown below:

In the Claims

Column 32, Lines 65 to 66, Claim 6 cancel the text "or a functionally equivalent fragment or variant thereof".

Column 33, Lines 3 to 4, Claim 7 cancel the text "or a functionally equivalent fragment or variant thereof".

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 26

<210> SEQ ID NO 1
<211> LENGTH: 31
<212> TYPE: PRT
<213> ORGANISM: Artificial Sequence
<220> FEATURE:
<223> OTHER INFORMATION: peptide molecule

<400> SEQUENCE: 1

Asp Gly Ser Val Val Val Asn Lys Val Ser Glu Leu Pro Ala Gly His
1               5                   10                  15

Gly Leu Asn Val Asn Thr Leu Ser Tyr Gly Asp Leu Ala Ala Asp
            20                  25                  30

<210> SEQ ID NO 2
<211> LENGTH: 13
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(1)
<223> OTHER INFORMATION: Xaa is absent or is selected from the group
      consisting of a beta alanine residue, 9-amino-3,6-dioxaoctanoic
      acid, and an acetyl group

<400> SEQUENCE: 2

Xaa His Gly Leu Asn Val Asn Thr Leu Ser Tyr Gly Asp
1               5                   10

<210> SEQ ID NO 3
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (12)..(12)
<223> OTHER INFORMATION: NH2 group

<400> SEQUENCE: 3

Asp Gly Ser Val Val Val Asn Lys Val Ser Glu Leu
1               5                   10
```

```
<210> SEQ ID NO 4
<211> LENGTH: 22
<212> TYPE: PRT
<213> ORGANISM: Artificial Sequence
<220> FEATURE:
<223> OTHER INFORMATION: peptide molecule

<400> SEQUENCE: 4

Ser Glu Leu Pro Ala Gly His Gly Leu Asn Val Asn Thr Leu Ser Tyr
1               5                   10                  15

Gly Asp Leu Ala Ala Asp
            20

<210> SEQ ID NO 5
<211> LENGTH: 15
<212> TYPE: PRT
<213> ORGANISM: Artificial Sequence
<220> FEATURE:
<223> OTHER INFORMATION: peptide molecule

<400> SEQUENCE: 5

Ser Glu Leu Pro Ala Gly His Gly Leu Asn Val Asn Thr Leu Ser
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (12)..(12)
<223> OTHER INFORMATION: NH2 group

<400> SEQUENCE: 6

Pro Ala Gly His Gly Leu Asn Val Asn Thr Leu Ser
1               5                   10

<210> SEQ ID NO 7
<211> LENGTH: 28
<212> TYPE: PRT
<213> ORGANISM: Artificial Sequence
<220> FEATURE:
<223> OTHER INFORMATION: peptide molecule

<400> SEQUENCE: 7

Val Val Val Asn Lys Val Ser Glu Leu Pro Ala Gly His Gly Leu Asn
1               5                   10                  15

Val Asn Thr Leu Ser Tyr Gly Asp Leu Ala Ala Asp
            20                  25

<210> SEQ ID NO 8
<211> LENGTH: 25
<212> TYPE: PRT
<213> ORGANISM: Artificial Sequence
<220> FEATURE:
<223> OTHER INFORMATION: peptide molecule

<400> SEQUENCE: 8

Asn Lys Val Ser Glu Leu Pro Ala Gly His Gly Leu Asn Val Asn Thr
1               5                   10                  15

Leu Ser Tyr Gly Asp Leu Ala Ala Asp
            20                  25
```

-continued

```
<210> SEQ ID NO 9
<211> LENGTH: 19
<212> TYPE: PRT
<213> ORGANISM: Artificial Sequence
<220> FEATURE:
<223> OTHER INFORMATION: peptide molecule

<400> SEQUENCE: 9

Pro Ala Gly His Gly Leu Asn Val Asn Thr Leu Ser Tyr Gly Asp Leu
1               5                   10                  15

Ala Ala Asp

<210> SEQ ID NO 10
<211> LENGTH: 16
<212> TYPE: PRT
<213> ORGANISM: Artificial Sequence
<220> FEATURE:
<223> OTHER INFORMATION: peptide molecule

<400> SEQUENCE: 10

His Gly Leu Asn Val Asn Thr Leu Ser Tyr Gly Asp Leu Ala Ala Asp
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(1)
<223> OTHER INFORMATION: Xaa is absent or is selected from the group
      consisting of a beta alanine residue, 9-amino-3,6-dioxaoctanoic
      acid, and an acetyl group
<220> FEATURE:
<221> NAME/KEY: MISC_FEATURE
<222> LOCATION: (13)..(13)
<223> OTHER INFORMATION: NH2 group

<400> SEQUENCE: 11

Xaa His Gly Leu Asn Val Asn Thr Leu Ser Tyr Gly Asp
1               5                   10

<210> SEQ ID NO 12
<211> LENGTH: 13
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(1)
<223> OTHER INFORMATION: X is absent or is selected from the group
      consisting of a beta alanine residue, 9-amino-3,6-dioxaoctanoic
      acid, and an acetyl group
<220> FEATURE:
<221> NAME/KEY: MISC_FEATURE
<222> LOCATION: (2)..(2)
<223> OTHER INFORMATION: D-amino acid residue
<220> FEATURE:
<221> NAME/KEY: MISC_FEATURE
<222> LOCATION: (4)..(11)
<223> OTHER INFORMATION: D-amino acid residue
<220> FEATURE:
<221> NAME/KEY: MISC_FEATURE
<222> LOCATION: (13)..(13)
<223> OTHER INFORMATION: D-amino acid residue
<220> FEATURE:
<221> NAME/KEY: MISC_FEATURE
<222> LOCATION: (13)..(13)
<223> OTHER INFORMATION: NH2 group
```

<400> SEQUENCE: 12

Xaa Asp Gly Tyr Ser Leu Thr Asn Val Asn Leu Gly His
1               5                   10

<210> SEQ ID NO 13
<211> LENGTH: 13
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(1)
<223> OTHER INFORMATION: X is absent or is selected from the group
      consisting of a beta alanine residue, 9-amino-3,6-dioxaoctanoic
      acid, and an acetyl group
<220> FEATURE:
<221> NAME/KEY: MISC_FEATURE
<222> LOCATION: (2)..(2)
<223> OTHER INFORMATION: D-amino acid residue
<220> FEATURE:
<221> NAME/KEY: MISC_FEATURE
<222> LOCATION: (4)..(11)
<223> OTHER INFORMATION: D-amino acid residue
<220> FEATURE:
<221> NAME/KEY: MISC_FEATURE
<222> LOCATION: (13)..(13)
<223> OTHER INFORMATION: D-amino acid residue
<220> FEATURE:
<221> NAME/KEY: MISC_FEATURE
<222> LOCATION: (13)..(13)
<223> OTHER INFORMATION: NH2 group

<400> SEQUENCE: 13

Xaa His Gly Leu Asn Val Asn Thr Leu Ser Tyr Gly Asp
1               5                   10

<210> SEQ ID NO 14
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (12)..(12)
<223> OTHER INFORMATION: D-amino acid residue
<220> FEATURE:
<221> NAME/KEY: MISC_FEATURE
<222> LOCATION: (12)..(12)
<223> OTHER INFORMATION: NH2 group

<400> SEQUENCE: 14

His Gly Leu Asn Val Asn Thr Leu Ser Tyr Gly Asp
1               5                   10

<210> SEQ ID NO 15
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (12)..(12)
<223> OTHER INFORMATION: D-amino acid residue

```
<220> FEATURE:
<221> NAME/KEY: MISC_FEATURE
<222> LOCATION: (12)..(12)
<223> OTHER INFORMATION: NH2 group

<400> SEQUENCE: 15

His Gly Leu Asn Val Asn Thr Leu Ser Tyr Gly Asp
1               5                   10

<210> SEQ ID NO 16
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (12)..(12)
<223> OTHER INFORMATION: NH2 group

<400> SEQUENCE: 16

His Gly Leu Asn Val Asn Thr Leu Ser Tyr Gly Asp
1               5                   10

<210> SEQ ID NO 17
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (12)..(12)
<223> OTHER INFORMATION: NH2 group

<400> SEQUENCE: 17

His Gly Leu Asn Val Asn Thr Leu Ser Tyr Gly Asp
1               5                   10

<210> SEQ ID NO 18
<211> LENGTH: 13
<212> TYPE: PRT
<213> ORGANISM: Artificial Sequence
<220> FEATURE:
<223> OTHER INFORMATION: peptide molecule
<220> FEATURE:
<221> NAME/KEY: MOD_RES
<222> LOCATION: (1)..(1)
<223> OTHER INFORMATION: bAla
<220> FEATURE:
<221> NAME/KEY: MISC_FEATURE
<222> LOCATION: (13)..(13)
<223> OTHER INFORMATION: NH2 group

<400> SEQUENCE: 18

Xaa His Gly Leu Asn Val Asn Thr Leu Ser Tyr Gly Asp
1               5                   10

<210> SEQ ID NO 19
<211> LENGTH: 12
<212> TYPE: PRT
<213> ORGANISM: Artificial Sequence
<220> FEATURE:
<223> OTHER INFORMATION: peptide molecule
```

```
<220> FEATURE:
<221> NAME/KEY: MISC_FEATURE
<222> LOCATION: (1)..(1)
<223> OTHER INFORMATION: Ac group
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (3)..(10)
<223> OTHER INFORMATION: D-amino acid residue
<220> FEATURE:
<221> NAME/KEY: MISC_FEATURE
<222> LOCATION: (12)..(12)
<223> OTHER INFORMATION: D-amino acid residue
<220> FEATURE:
<221> NAME/KEY: MISC_FEATURE
<222> LOCATION: (12)..(12)
<223> OTHER INFORMATION: NH2 group

<400> SEQUENCE: 19

Asp Gly Tyr Ser Leu Thr Asn Val Asn Leu Gly His
1               5                   10

<210> SEQ ID NO 20
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(1)
<223> OTHER INFORMATION: Ac group
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (3)..(10)
<223> OTHER INFORMATION: D-amino acid residue
<220> FEATURE:
<221> NAME/KEY: MISC_FEATURE
<222> LOCATION: (12)..(12)
<223> OTHER INFORMATION: D-amino acid residue
<220> FEATURE:
<221> NAME/KEY: MISC_FEATURE
<222> LOCATION: (12)..(12)
<223> OTHER INFORMATION: NH2 group

<400> SEQUENCE: 20

His Gly Leu Asn Val Asn Thr Leu Ser Tyr Gly Asp
1               5                   10

<210> SEQ ID NO 21
<211> LENGTH: 13
<212> TYPE: PRT
<213> ORGANISM: Artificial Sequence
<220> FEATURE:
<223> OTHER INFORMATION: peptide molecule
<220> FEATURE:
<221> NAME/KEY: MOD_RES
<222> LOCATION: (13)..(13)
<223> OTHER INFORMATION: bAla-NH2

<400> SEQUENCE: 21

His Gly Leu Asn Val Asn Thr Leu Ser Tyr Gly Asp Xaa
1               5                   10
```

```
<210> SEQ ID NO 22
<211> LENGTH: 14
<212> TYPE: PRT
<213> ORGANISM: Artificial Sequence
<220> FEATURE:
<223> OTHER INFORMATION: peptide molecule
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (14)..(14)
<223> OTHER INFORMATION: bAla-NH2

<400> SEQUENCE: 22

Xaa His Gly Leu Asn Val Asn Thr Leu Ser Tyr Gly Asp Xaa
1               5                   10

<210> SEQ ID NO 23
<211> LENGTH: 15
<212> TYPE: PRT
<213> ORGANISM: Artificial Sequence
<220> FEATURE:
<223> OTHER INFORMATION: peptide molecule

<400> SEQUENCE: 23

Gly Leu Asn Val Asn Thr Leu Ser Tyr Gly Asp Leu Ala Ala Asp
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(1)
<223> OTHER INFORMATION: O2Oc
<220> FEATURE:
<221> NAME/KEY: MISC_FEATURE
<222> LOCATION: (12)..(12)
<223> OTHER INFORMATION: NH2 group

<400> SEQUENCE: 24

His Gly Leu Asn Val Asn Thr Leu Ser Tyr Gly Asp
1               5                   10

<210> SEQ ID NO 25
<211> LENGTH: 12
<212> TYPE: PRT
<213> ORGANISM: Artificial Sequence
<220> FEATURE:
<223> OTHER INFORMATION: peptide molecule
<220> FEATURE:
<221> NAME/KEY: MISC_FEATURE
<222> LOCATION: (1)..(12)
<223> OTHER INFORMATION: Cyclic peptide

<400> SEQUENCE: 25

His Gly Leu Asn Val Asn Thr Leu Ser Tyr Gly Asp
1               5                   10

<210> SEQ ID NO 26
<211> LENGTH: 11
<212> TYPE: PRT
<213> ORGANISM: Artificial Sequence
<220> FEATURE:
<223> OTHER INFORMATION: amino acid sequence inverted for peptide
      molecule
```

```
<400> SEQUENCE: 26

Gly Leu Asn Val Asn Thr Leu Ser Tyr Gly Asp
1               5                   10
```